(12) United States Patent
Berik et al.

(10) Patent No.: US 7,446,867 B2  
(45) Date of Patent: Nov. 4, 2008

(54) METHOD AND APPARATUS FOR DETECTION AND ANALYSIS OF BIOLOGICAL MATERIALS THROUGH LASER INDUCED FLUORESCENCE

(76) Inventors: Jevgeni Berik, Pallase puiestee 125 Box 2, Tartu (EE) 51011; Ants Kurg, Kalevi 65, Tartu (EE) 51011; Andres Metspalu, Liivakuru 3, Tartu (EE) 50304

(*) Notice: Subject to any disclaimer, the term of this patent is extended or adjusted under 35 U.S.C. 154(b) by 0 days.

(21) Appl. No.: 11/584,934

(22) Filed: Oct. 23, 2006

(65) Prior Publication Data  
US 2007/0091306 A1 Apr. 26, 2007

Related U.S. Application Data

(60) Provisional application No. 60/729,591, filed on Oct. 24, 2005.

(51) Int. Cl.  
*G01N 21/64* (2006.01)

(52) U.S. Cl. .................... 356/317; 356/318; 356/417; 250/458.1

(58) Field of Classification Search .................. 356/317, 356/318, 417; 250/458.1, 459.1, 461.1, 461.2  
See application file for complete search history.

(56) References Cited

U.S. PATENT DOCUMENTS

| 6,140,653 A | 10/2000 | Che |
| 6,614,031 B2 * | 9/2003 | Engelhardt et al. ....... 250/458.1 |
| 2004/0012676 A1 | 1/2004 | Weiner et al. |
| 2006/0170916 A1 * | 8/2006 | Voigt et al. .................. 356/301 |

FOREIGN PATENT DOCUMENTS

EE 9900072 12/2000

* cited by examiner

*Primary Examiner*—F. L Evans  
(74) *Attorney, Agent, or Firm*—Dodds & Associates; John Dodds; Susanne Somersalo

(57) ABSTRACT

The present invention provides a method and an apparatus to analyze fast and accurately biological samples. The method includes prior mapping of the DNA chip with a CCD camera, addressed excitation of samples, and recording of fluorescence spectra via ultra-fast spectrometer.

9 Claims, 1 Drawing Sheet

METHOD AND APPARATUS FOR DETECTION AND ANALYSIS OF BIOLOGICAL MATERIALS THROUGH LASER INDUCED FLUORESCENCE

CROSS REFERENCE TO RELATED APPLICATIONS

This non-provisional patent application claims priority of the US provisional patent application number 60/729,591 filed on Oct. 24, 2005.

TECHNICAL FIELD OF THE INVENTION

This invention belongs to the field of detection methods and equipment, based on detection of laser induced fluorescence (LIF) of various materials, more specifically biological materials and analysis thereof.

BACKGROUND

Several different methods (e.g. spectral measurements in infrared, visible and ultraviolet region, polarisation, phase and impulse characteristics measurements, colorimetry, radiation pyrometry; etc.) for the study and analysis of chemical and physical properties of biological materials are known, along with corresponding equipment.

Various approaches, that utilise methods and equipment based on the recording of fluorescence for the detection and analysis of biological materials such as DNA, are more widely known. A system and a method for detection of laser-induced fluorescence (LIF) of a biological sample is also described in US patent application US 20040012676.

Classical equipments for reading DNA chips—detectors and scanners—have two main shortcomings. First shortcoming is the low reading speed, as these apparatuses successively read the whole surface of a DNA chip. This includes areas with biological samples, as well as empty regions. Second shortcoming is that, when a point is read, its spectral characteristics are only measured in one or two points of the spectrum, which can lead to detection errors.

According to currently known approaches for the determination of the composition of a material on a carrier surface the surface is irradiated with a focused laser beam, and the resulting LIF is registered. If the surface properties have spatial difference, then the laser beam scans the carrier's surface and the intensity of the LIF is measured in each subsequent point. The total measurement time is determined by the speed of sample repositioning and the surface area to be studied.

In order to increase amount of information (or detection selectivity), a spectral filter may be placed before the element recording a fluorescence radiation, to separate certain part of the spectrum. However, to obtain adequate information about a structure of material under investigation, different filters have to be used for different wavelengths, and several consecutive scans have to be made of the object. This clearly prolongs the measurement duration in proportion with the number of wavelengths studied (i.e. filters used). The latter could be considered the primary flaw of currently known approaches and there is a need for a system that allows faster analysis without lowering the accuracy of the measurements.

Known approaches further include, for instance, U.S. Pat. No. 6,140,653, which describes an apparatus that utilises a CCD camera as an array detector for analysing a biological sample excited by white light by reading its fluorescence radiation.

The level of technology is also presented in Estonian patent application publication EE9900072 that describes an apparatus and a method for parallel detection and analysis of biopolymeric molecules marked by fluorescence markers on a two-dimensional array on a surface of thin transparent carrier. Laser beam directed into the carrier spreads within it due to the condition of total internal reflection (TIR). A certain amount of radiation (evanescent wave) exits through the surface of carrier and excites LIF of the fluorophores in the composition on biopolymeric molecules on the surface of the matrix. LIF is detected by a photosensitive element (CCD camera), providing information about fluorescent molecules bound to the matrix carrier.

SUMMARY OF THE INVENTION

From the above said it is evident that there is a clear need for a faster and more accurate method and related apparatus for detection and analysis of biological material.

Accordingly, it is a general object of the current invention to provide a fast and accurate method and apparatus for detection and analysis of biological material.

Another object of the current invention is to provide a method and an apparatus for the detection and analysis of biological materials using LIF with high detection speed, selectivity and sensitivity.

A further object of the current invention is to allow essentially reduced measurement time while simultaneously maintaining or increasing selectivity of data recording and increasing reliability of analysis of biological material.

Unlike approaches known so far, where samples across the entire chip area are consecutively excited by focused spot of light at scanning and LIF signal is recorded by a photomultiplier or alternatively LIF is collected using a CCD camera, the present invention provides a remarkable advantage of increased speed, achieved through several inventive steps in technical solutions. The method and apparatus according to the current inventions includes prior mapping of the DNA chip with a CCD camera, addressed excitation of samples, and recording of fluorescence spectra via ultra-fast acousto-optical spectrometry.

DETAILED DESCRIPTION OF THE INVENTION

Figure 1:
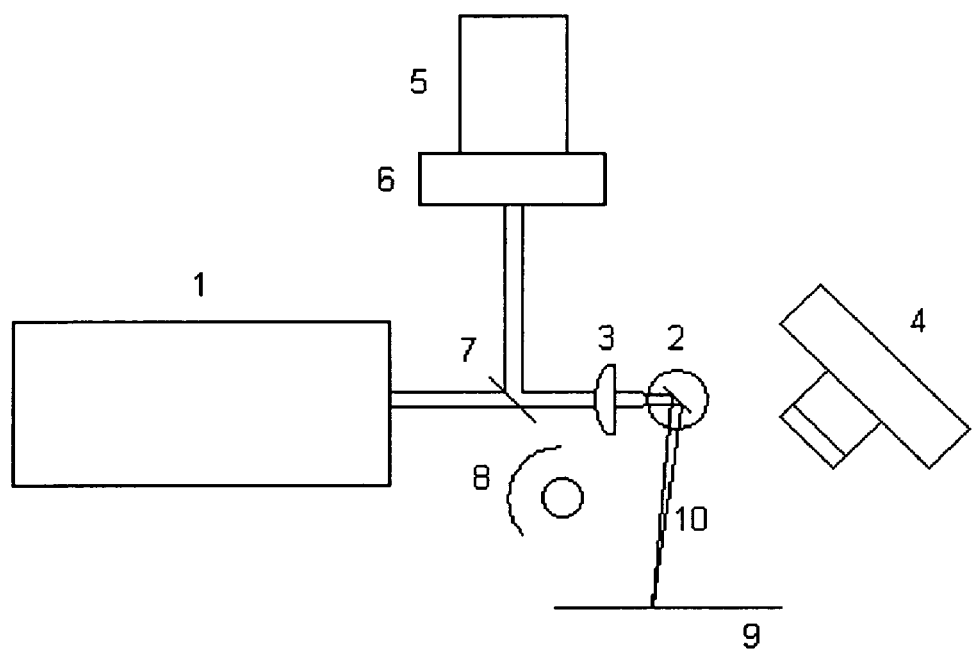
FIG. 1 illustrates one embodiment of the apparatus according to this disclosure for the detection and analysis of biological materials.

The analysis of biological materials is subject to low sensitivity, selectivity and speed of detection. The purpose of the method and apparatus of the present invention for the detection and analysis of biological materials using LIF is to provide a solution that has a higher speed, selectivity and sensitivity of detection than approaches known so far. The primary advantage of the apparatus and method of this invention is the speed and accuracy achieved through prior mapping of the matrix of probes on carrier (e.g. a DNA chip) with a CCD camera, addressed excitation of samples, and recording of fluorescence spectra via acousto-optical spectrometry. The inventive steps of the current disclosure allow essentially reduced measurement time while simultaneously maintaining or increasing selectivity of data recording and increasing reliability.

For detection and analysis of biological material according to the current disclosure, the sample point locations on a chip are first mapped with a CCD camera, by irradiating the chip with any light source and recording the sample point locations on the chip on the basis of spectrally broadband fluorescence or any other optical characteristics (scattering, transmittance or reflectance). This information is recorded with a computer, and by processing this information, the spatial co-ordinates of the samples are determined.

After mapping the chip the addressed excitation of samples is carried out by directing a focused laser beam consecutively at all necessary sample points; the time spent on this is related only to sample excitation and recording of LIF only from the samples studied. For LIF recording, the apparatus and the method of the present invention use an adjustable-wavelength filter, for instance an acousto-optical, an electro-optical filter, or some other fast spectral instrument that allows for a quick spectral analysis of fluorescence radiation. According to a most preferred embodiment the filter is an acousto-optical filter.

The operating principle of the acusto-optical (AO) filter is based on creation of dynamic diffracted light beam in a crystal optical element, which is affected by high frequency mechanical vibration (for instance ultrasound). As the diffracted beam direction is deviated from the entrance beam and the beam has polarization orthogonal it is possible to achieve a situation, where only the narrow spectral range corresponding to the frequency of the driving signal presents in the output and this element operates like a tunable spectral filter.

Other spectral components are cut off by spatial filtering or by crossed polarisers.

For scanning in the spectral range of visible light (400-700 nm) the ultrasound frequency has to be tuned in the range 50-300 MHz. Thus, a wavelength scan is performed by tuning the frequency of the driving ultrasound and the filter with the light detector (photomultiplier) after it is used as a spectrometer.

Spectral positions of the acousto-optical filter are set by the operator in units of ten to one hundred or more, depending on precision requirements, which depend on the measurement conditions. Since the acousto-optical filter has no moving parts, its switching speed from one spectral position to another is less than 10 microseconds. Adding to this the time directly needed for the measurement (approximately 5 microseconds), it is possible to measure spectra at twenty different wavelengths in 300 microseconds; this gives a speed of about 3000 spectra per second. After recording the fluorescence spectrum, the data is analysed on a computer by a special program and the physico-chemical properties of the sample are determined in the measured points.

The following example is meant to be descriptive and by no means limiting of the various embodiments of the present invention.

EXAMPLE

Now referring specifically to FIG. 1, the apparatus for the detection and analysis of biological materials (for instance DNA) comprises a laser 1, a spatial scanner 2, an objective 3, a CCD camera 4, a photomultiplier 5 and a fast tunable filter 6 (for instance an acousto-optical filter), that with a photomultiplier (PMP) 5 forms a spectrometer, a dichroitic beam splitter 7, a light source 8, and a sample carrier or chip 9, that has, for example, biological material samples placed on it as dots. The detection and analysis apparatus is connected to a computer (not shown in the drawing) where special programs control the apparatus, analyze the results and determine the physico-chemical properties of the sample.

Still referring to FIG. 1, the chip 9, along with sample dots, is placed in a suitable starting position for laser beam 10. Using the scanner 2, the beam 10 is directed sequentially at the samples to be studied. Fast tunable filter 6 is tuned so as to allow wavelengths $\lambda 1$, $\lambda 2$, etc through $\lambda i$ to pass through. For each position of the filter 6, fluorescence intensity is measured and the results are stored on a computer. After this, beam 10 is positioned in the next spatial position and the measurement cycle is repeated, until all positions of interest have been measured.

The resulting fluorescence spectra are processed to yield physico-chemical properties of fluorophores in the measured points.

Another embodiment of the present invention allows selecting specific sample points on the chip 9 and exciting with a laser beam 10 only these points, instead of scanning the entire surface of the chip 9. To determine the locations of these sample points, a flash picture is taken of the sample dots applied to the surface of the chip 9, illuminating it with a source of light 8, for instance a lamp or a scattered laser beam. CCD camera 4 then records a sample dot location on the surface of the chip 9. This information is used to create a virtual matrix of sample points on the surface of the chip 9, which is then used to guide laser beam 10 only to the points to be analysed. Since the number of spatial positions to be measured decreases, the total amount of time needed for measurements also decreases.

The spatial scanner 2 then directs serially the laser beam 10 only to the points under study. LIF spectrum is determined instantaneously for each point and spectral analysis of the point is then carried out.

Laser beam 10 can also be guided to a necessary position by using some other kind of scanner, for instance a mechanical one, instead of moving chip 9 and the sample dots under study.

What is claimed is:

1. A method for detection and analysis of biological materials by using laser induced fluorescence, said method comprising following steps:
    a) a focused laser beam is moved to a suitable position on a chip carrying a sample;
    b) a fast tunable filter is tuned so as to allow wavelengths $\lambda 1$, $\lambda 2$, through $\lambda i$, to pass through for registration;
    c) for each spectral position of the fast tunable filter, fluorescence intensity of the sample is measured;
    d) results are stored on a computer;
    e) laser beam is positioned in the next spatial position on the chip;
    f) steps b to e are repeated until all positions of interest have been measured and stored;
    g) resulting fluorescence spectra are processed; and
    h) physico-chemical properties of fluorophores are determined in each measured points.

2. The method according to claim 1, wherein the fast tunable filter is an acousto-optical filter.

3. The method according to claim 1, wherein prior to step a) location of the sample points on a chip are determined with a CCD camera and the laser beam is moved only to the determined locations on the chip.

4. A method for the detection and analysis of biological materials by using laser induced fluorescence, said method comprising steps of:
    a) illuminating a biological material sample with light source and recording optical characteristics of the sample with a CCD camera;

b) based on recorded characteristics creating a virtual matrix of co-ordinates of all sample points on chip surface;

c) moving by scanner a focused laser beam to any of sample points according to its virtual matrix position;

d) determining LIF spectrum instantaneously by fast spectrometer, said spectrometer consisting of a photomultiplier and an fast tunable filter;

e) carrying out spectral analysis of the point;

f) moving a focused laser beam to the next sample point and repeat a procedure up to the last required point.

5. The method according to claim 4, wherein the fast tunable filter is an acousto-optical filter.

6. The method for the detection and analysis of biological materials according to claim 4, wherein the excitation and measurement of fluorescence radiation spectrum are carried out within up to $1/1000$ of a second.

7. The method for the detection and analysis of biological materials according to claim 5, wherein the excitation and measurement of fluorescence radiation spectrum are carried out within up to $1/1000$ of a second.

8. An apparatus for applying detection and analysis of biological materials according to claim 4 by using laser excitation fluorescence, said apparatus comprising:

a light source to illuminate a biological material sample placed on a chip, in order to create recordable optical characters;

a CCD camera to record the optical characters for predetermination of sample point locations;

an interconnected laser to create a laser beam;

a spatial scanner to direct the laser beam at selected sample points; and a spectrometer for recording laser induced fluorescence emitted from the sample spots, said spectrometer consisting of a photomultiplier and an adjustable-wavelength filter having passing range of $\lambda 1$ through $\lambda i$, whereby fluorescence intensity at each selected wavelength is measured.

9. The apparatus for the detection and analysis of biological materials using laser excitation fluorescence according to claim 8, wherein the adjustable-wavelength filter is an acousto-optical filter.

\* \* \* \* \*